(12) United States Patent
Iwashita et al.

(10) Patent No.: US 12,350,109 B2
(45) Date of Patent: *Jul. 8, 2025

(54) ULTRASOUND PROBE

(71) Applicant: FUJIFILM Corporation, Tokyo (JP)

(72) Inventors: Takayuki Iwashita, Chiba (JP);
Hiroshi Hattori, Chiba (JP); Tomohiro Shiraishi, Chiba (JP); Hidetsugu Katsura, Chiba (JP); Wataru Sawada, Chiba (JP); Sachio Shimada, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 54 days.

This patent is subject to a terminal disclaimer.

(21) Appl. No.: 18/233,682

(22) Filed: Aug. 14, 2023

(65) Prior Publication Data

US 2024/0057980 A1    Feb. 22, 2024

(30) Foreign Application Priority Data

Aug. 22, 2022   (JP) ................. 2022-131776

(51) Int. Cl.
*A61B 8/00* (2006.01)
*B06B 1/06* (2006.01)
(52) U.S. Cl.
CPC ............ *A61B 8/546* (2013.01); *A61B 8/4488* (2013.01); *B06B 1/0622* (2013.01); *B06B 2201/76* (2013.01)

(58) Field of Classification Search
CPC ...... A61B 8/546; A61B 8/4455; A61B 8/4444; A61B 8/42
See application file for complete search history.

(56) References Cited

U.S. PATENT DOCUMENTS

| | | | |
|---|---|---|---|
| 9,943,287 B2 | 4/2018 | Sudol et al. | |
| 2015/0276685 A1* | 10/2015 | Yasuhara | G01N 29/24 73/632 |
| 2021/0113187 A1* | 4/2021 | Morita | A61B 8/4444 |
| 2024/0057973 A1 | 2/2024 | Iwashita et al. | |
| 2024/0057979 A1 | 2/2024 | Iwashita et al. | |
| 2024/0057981 A1 | 2/2024 | Iwashita et al. | |

FOREIGN PATENT DOCUMENTS

| | | |
|---|---|---|
| JP | 5972296 B2 | 8/2016 |
| JP | 2017-070449 A | 4/2017 |

* cited by examiner

*Primary Examiner* — Ashley K Buran
*Assistant Examiner* — Tommy T Ly
(74) *Attorney, Agent, or Firm* — Paul Teng (57) ABSTRACT

Behind an electronic circuit, a thermally anisotropic main backing is provided. The main backing has two outer surfaces (low thermal conductivity surfaces) perpendicular to an X direction. In a first gap located adjacent to one of the outer surfaces, an FPC and a first group of electric components are arranged. In a second gap located adjacent to the other one of the outer surfaces, the FPC and a second group of electric components are arranged.

18 Claims, 10 Drawing Sheets

ULTRASOUND PROBE

CROSS REFERENCE TO RELATED APPLICATION

This application claims priority to Japanese Patent Application No. 2022-131776 filed on Aug. 22, 2022, which is incorporated herein by reference in its entirety including the specification, claims, drawings, and abstract.

TECHNICAL FIELD

The present disclosure relates to an ultrasound probe, and more particularly to a heat transfer structure inside an ultrasound probe.

BACKGROUND

In an ultrasonic examination, an ultrasonic diagnosis apparatus is used. An ultrasonic diagnosis apparatus comprises an ultrasound probe that performs transmission and reception of ultrasound waves. In recent years, use of an ultrasound probe having a two-dimensional transducer array is becoming widespread. Such an ultrasound probe is referred to as a three-dimensional probe or a 2D array probe. By using a 2D array probe, a set of volume data can be obtained by performing a two-dimensional scanning of an ultrasound beam, or a set of frame data can be obtained by performing a one-dimensional scanning of an ultrasound beam to which two-dimensional electronic focusing is applied.

Inside an ultrasound probe, a transducer assembly including a transducer array is provided. The transducer assembly typically comprises a matching layer provided in front of the transducer array (i.e., on a side toward a subject's living body), and a backing provided behind the transducer array (i.e., on a side away from the living body). The backing serves to attenuate unnecessary ultrasound waves emitted rearward from the transducer array.

In the 2D array probe noted above, a transducer assembly typically comprises a two-dimensional transducer array and an electronic circuit. In the electronic circuit, transmission signals to be supplied to transducers are generated, and reception signals output from the transducers are processed. The electronic circuit is normally composed of one or a plurality of integrated circuits (or more specifically, one or a plurality of ASICs (application-specific integrated circuits)).

In a 2D array probe, a considerable amount of heat is generated in the two-dimensional transducer array and the electronic circuit. In particular, heat is generated in the electronic circuit in a large amount. From the perspective of safety of a subject's living body, it is necessary to maintain the temperature of an ultrasound transmission/reception surface of the ultrasound probe to or below a specified temperature. In order to effectively dissipate heat generated in the electronic circuit and the like to outside, a heat transfer structure is provided inside the ultrasound probe.

An ultrasound probe disclosed in Document 1 (JP 5972296 B) includes a transducer array, an ASIC, and a backing, which are vertically stacked. Document 1 nowhere describes any heat transfer structure that makes use of a thermal anisotropic property possessed by a backing. An ultrasound probe disclosed in Document 2 (JP 2017-70449 A) includes a backing with a lead array embedded therein, and an electronic circuit is provided behind the backing. Document 2 nowhere describes any backing provided behind the electronic circuit.

SUMMARY

The present disclosure is directed to, in an ultrasound probe, reserving space for arranging components near side surfaces of a backing. Alternatively, the present disclosure is directed to, in an ultrasound probe, allowing heat-sensitive components to be provided at positions near side surfaces of a backing.

An ultrasound probe according to an aspect of the present disclosure includes a transducer array, an electronic circuit provided behind the transducer array and electrically connected to the transducer array, a sheet-shaped wiring member electrically connected to the electronic circuit, a backing provided behind the electronic circuit and configured to attenuate ultrasound waves from the transducer array, and a heat absorbing member configured to absorb heat from the backing. Assuming that a direction in which the transducer array, the electronic circuit, and the backing are arranged is defined as a Z direction, a direction perpendicular to the Z direction is defined as an X direction, and a direction perpendicular to the Z direction and the X direction is defined as a Y direction, in the backing, both of Z-direction thermal conductivity and Y-direction thermal conductivity are higher than X-direction thermal conductivity. The backing has two outer surfaces intersecting the X direction and bordering a first gap and a second gap, and the wiring member extends through the first gap and the second gap.

BRIEF DESCRIPTION OF DRAWINGS

Embodiment(s) of the present disclosure will be described based on the following figures, wherein.

DESCRIPTION OF EMBODIMENTS

Embodiments will now be described by reference to the drawings.

(1) Overview of Embodiments

An ultrasound probe according to an embodiment includes a transducer array, an electronic circuit, a wiring member, a backing, and a heat absorbing member. The electronic circuit is provided behind the transducer array. The electronic circuit is a circuit electrically connected to the transducer array. The wiring member is a sheet-shaped member electrically connected to the electronic circuit. The backing is provided behind the electronic circuit. In the backing, ultrasound waves from the transducer array are attenuated. The heat absorbing member is a member that absorbs heat from the backing. In the backing, both of Z-direction thermal conductivity and Y-direction thermal conductivity are higher than X-direction thermal conductivity. The backing has two outer surfaces intersecting the X direction and bordering a first gap and a second gap. The wiring member extends through the first gap and the second gap. Here, the Z direction is a direction in which the transducer array, the electronic circuit, and the backing are arranged. A direction perpendicular to the Z direction is the X direction, and a direction perpendicular to the Z direction and the X direction is the Y direction.

In the above configuration, each of two outer surfaces of the backing intersecting the Y direction is, in relative terms, a high thermal conductivity surface, and each of the two outer surfaces of the backing intersecting the X direction is, in relative terms, a low thermal conductivity surface. According to the above configuration, the first gap and the second gap for allowing the wiring member to extend therethrough can be reserved around the backing. Since both of the two outer surfaces bordering the first gap and the second gap are low thermal conductivity surfaces, components arranged in the first gap and the second gap (for example, groups of electric components provided on the wiring member) can be thermally protected. The above-described backing corresponds to the main backing described later.

In an embodiment, the wiring member has a horizontal part, a first vertical portion, and a second vertical portion. The horizontal part is a part provided between the transducer array and the electronic circuit. The first vertical portion is a portion connected to one end portion of the horizontal part via a first bent portion. The second vertical portion is a portion connected to the other end portion of the horizontal part via a second bent portion. The first vertical portion extends through the first gap. The second vertical portion extends through the second gap.

An ultrasound probe according to an embodiment comprises a first group of electric components arranged on the first vertical portion and received in the first gap, and a second group of electric components arranged on the second vertical portion and received in the second gap. According to this configuration, the first group of electric components and the second group of electric components can be arranged at positions near the electronic circuit. Each of the electric components is thermally protected as described above. The first group of electric components and the second group of electric components perform functions necessary for operation of the electronic circuit. Each of the first group of electric components and the second group of electric components includes capacitors. The capacitors are thermally protected.

In an embodiment, the two outer surfaces intersecting the X direction are a first outer surface and a second outer surface. The first vertical portion has a first face side which faces the first outer surface and on which the first group of electric components are arranged, and a first back side located opposite to the first face side. The second vertical portion has a second face side which faces the second outer surface and on which the second group of electric components are arranged, and a second back side located opposite to the second face side. A first electrical insulation member is provided between the first outer surface and the first group of electric components. A second electrical insulation member is provided between the second outer surface and the second group of electric components.

According to the above configuration, it is possible to use an electrically conductive backing. In other words, in cases where such a backing is used, the first group of electric components and the second group of electric components can be electrically protected.

An ultrasound probe according to an embodiment comprises a first reinforcement member joined to the first back side, and a second reinforcement member joined to the second back side. According to this configuration, strength of the first vertical portion and the second vertical portion can be increased.

In an embodiment, the backing has two outer surfaces intersecting the Y direction. The heat absorbing member has two inner surfaces joined to the two outer surfaces intersecting the Y direction. Each of the two outer surfaces intersecting the Y direction is a high thermal conductivity surface. Accordingly, with this configuration, efficiency of heat transfer from the backing to the heat absorbing member can be increased.

(2) Details of Embodiments

Figure 1:
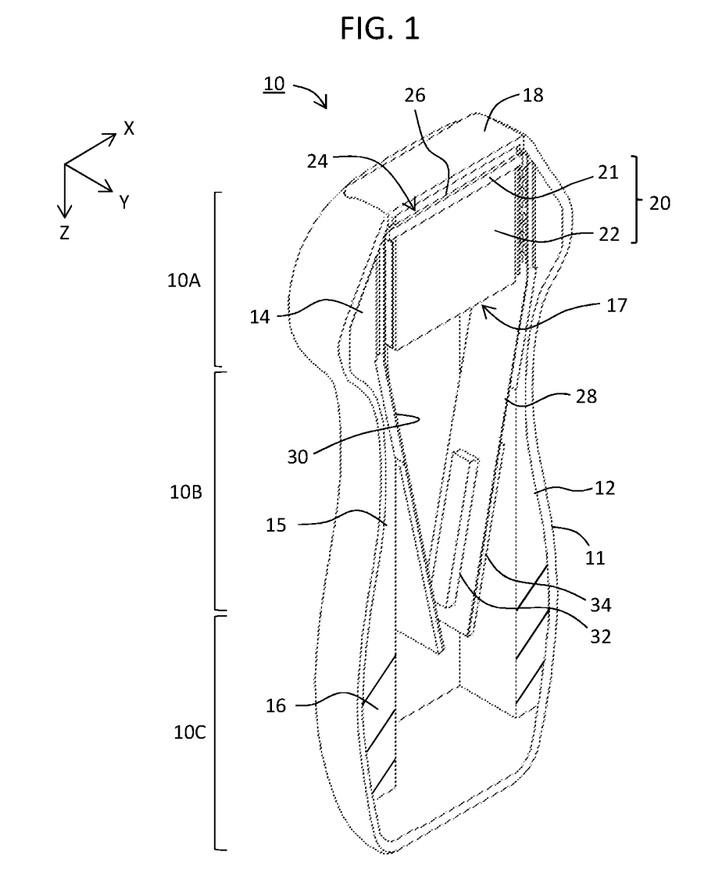
FIG. 1 is a cross-sectional view showing a structure of an ultrasound probe according to an embodiment.

FIG. 1 shows an ultrasound probe 10 according to an embodiment. The ultrasound probe 10 is to be connected to an ultrasonic diagnosis apparatus main body, which is not shown in the drawing. The ultrasound probe 10 and the ultrasonic diagnosis apparatus main body constitute an ultrasonic diagnosis apparatus. The ultrasonic diagnosis apparatus is a medical apparatus used for ultrasonic examination of a subject (i.e., a living body). The ultrasound probe 10 includes a cable and a connector, which are not shown in the drawing.

In FIG. 1, an X direction is a first horizontal direction, a Y direction is a second horizontal direction, and a Z direction is a vertical direction. The three directions have a perpendicular relationship to each other. A central axis of the ultrasound probe 10 is parallel to the Z direction. The X direction is a first electronic scan direction, and the Y direction is a second electronic scan direction.

In FIG. 1, an XZ cross section of the ultrasound probe 10 is shown. It should be noted, however, that illustration of part of the configuration of the ultrasound probe 10 is omitted. The ultrasound probe 10 is formed having a tip part 10A, a middle part 10B, and a rear end part 10C. The tip part 10A is a part having an enlarged size, and the middle part 10B is a part having a narrowed portion.

A shell 12 is provided inside a resin housing 11. The shell 12 is a heat absorbing member. The shell 12 is composed of, for example, a metal having good thermal conductivity, or more specifically, a metal such as aluminum. The shell 12 is formed having a shell head (or tip part) 14, a middle part 15, and a rear end part 16. The shell 12 is a hollow member, and has a shape that surrounds a cavity (or internal space) having the shape of a rectangular prism. At each position along the Z direction, an XY cross section of the cavity is rectangular. Outer surfaces of the shell 12 and inner surfaces of the resin housing 11 are in close contact with each other.

Inside the shell head 14, a transducer assembly 17 is arranged. The transducer assembly 17 comprises, in addition to a two-dimensional transducer array, a backing member (or a set of backings) 20 configured to attenuate unnecessary ultrasound waves. In the example configuration shown in the drawing, the backing member 20 includes an auxiliary backing (or first backing) 21 and a main backing (or second backing) 22. Both of the auxiliary backing 21 and the main backing 22 are composed of a backing having thermal anisotropy. The auxiliary backing 21 has a first thermal anisotropic property, and the main backing 22 has a second thermal anisotropic property different from the first thermal anisotropic property. This point will be described later in detail. The stacking direction in the transducer assembly 17 is the Z direction.

The transducer assembly 17 comprises a laminate member containing the two-dimensional transducer array, and an electronic circuit composed of a plurality of ICs. The upper surface of the transducer assembly 17 is covered with a protective layer 18. The surface of the protective layer 18 is an ultrasound transmission/reception surface placed into contact with a surface of a subject.

An FPC (or flexible circuit or flexible circuit board) 24 is provided between the laminate member and the electronic circuit. The FPC 24 is a flexible, sheet-shaped wiring member. In the present embodiment, the FPC 24 is a multilayer FPC having a plurality of wiring layers. The thickness of the FPC 24 is, for example, within a range from 0.1 to 0.5 mm. The width of the FPC 24 in the Y direction is, for example, within a range from 10 to 20 mm.

The FPC 24 has a horizontal part 26, a first hanging part 28, and a second hanging part 30. On each of the first hanging part 28 and the second hanging part 30, a plurality of connectors 32 and reinforcement plates 34 are provided. The upper end portion of the first hanging part 28 is a first vertical portion. The upper end portion of the second hanging part 30 is a second vertical portion.

Figure 2:
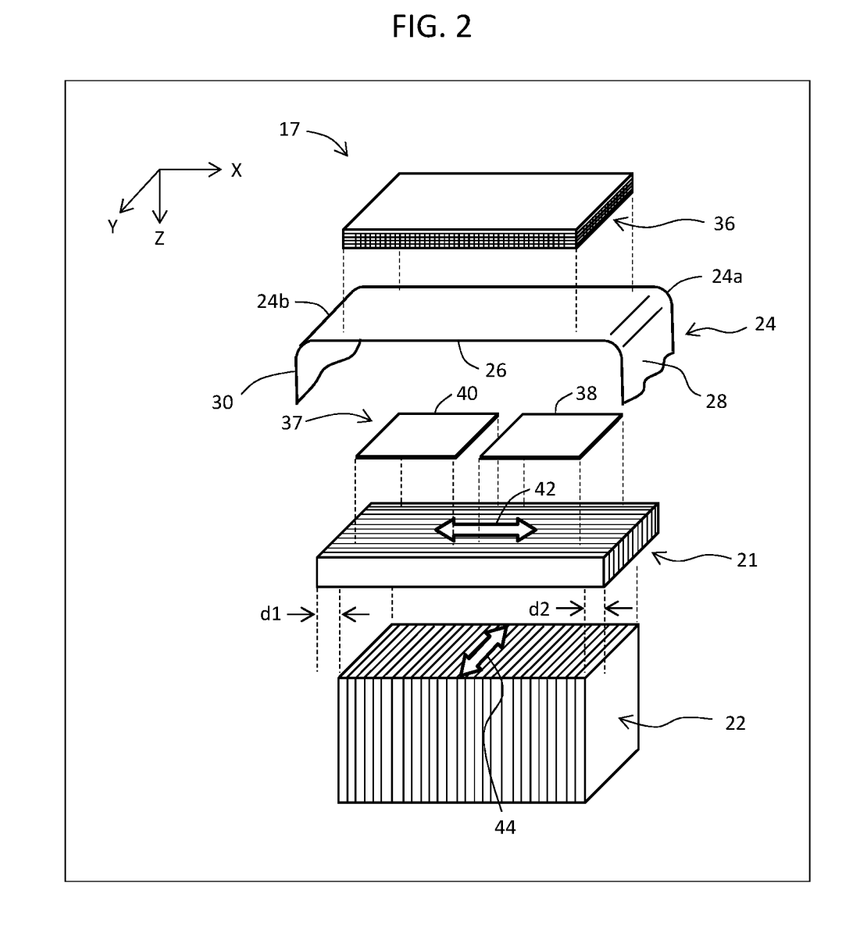
FIG. 2 is an exploded perspective view showing a transducer assembly.

FIG. 2 shows a configuration of the transducer assembly 17. As noted earlier, the transducer assembly 17 comprises a laminate member 36 containing the two-dimensional transducer array. An electronic circuit 37 is provided behind the laminate member 36 (i.e., on a side away from the living body). The electronic circuit 37 is composed of, for example, two ICs 38, 40 arranged in the X direction. Each of the ICs 38, 40 has a function of generating transmission signals to be supplied to the two-dimensional transducer array, and a function of processing reception signals from the two-dimensional transducer array. The latter function includes a sub-beam forming function. The electronic circuit 37 may be composed of a larger number of ICs arranged in the X direction and the Y direction.

The two-dimensional transducer array is composed of a plurality of transducers arranged in the first electronic scan direction (or the X direction) and the second electronic scan direction (or the Y direction). For example, the two-dimensional transducer array is composed of some tens, hundreds, thousands, ten thousands, or a greater number of transducers. Instead of the two-dimensional transducer array, a one-dimensional transducer array may be provided. The one-dimensional transducer array is composed of a plurality of transducers arranged in the X direction.

Between the laminate member 36 and the electronic circuit 37, the horizontal part 26 of the FPC 24 is sandwiched. The horizontal part 26 performs a signal connecting function, a wiring pattern converting function, and the like. One end portion of the horizontal part 26 is connected to the first hanging part 28 via a first bent portion 24a. The other end portion of the horizontal part 26 is connected to the second hanging part 30 via a second bent portion 24b. A central axis of the horizontal part 26 is parallel to the X direction. In other words, the direction in which the first hanging part 28, the horizontal part 26, and the second hanging part 30 are arranged is the X direction.

The auxiliary backing 21 has a plate shape. The auxiliary backing 21 is configured to exhibit an effect of attenuating unnecessary ultrasound waves radiated rearward from the two-dimensional transducer array. The auxiliary backing 21 has a first thermal anisotropic property. More specifically, in the auxiliary backing 21, each of Z-direction thermal conductivity and X-direction thermal conductivity is higher than Y-direction thermal conductivity.

The auxiliary backing 21 exhibits a heat transfer effect in the Z direction. Further, as shown by reference numeral 42, the auxiliary backing 21 exhibits an effect of diffusing heat in the X direction. The upper surface of the auxiliary backing 21 is joined to the electronic circuit 37, and the lower surface of the auxiliary backing 21 is joined to the upper surface of the main backing 22.

The main backing 22 has a rectangular solid shape. The main backing 22 is configured to exhibit an effect of attenuating unnecessary ultrasound waves entering via the auxiliary backing. The main backing 22 has a second thermal anisotropic property different from the above-described first thermal anisotropic property. More specifically, in the main backing 22, each of Z-direction thermal conductivity and Y-direction thermal conductivity is higher than X-direction thermal conductivity.

The main backing 22 performs, in addition to a heat transfer function in the Z direction, a heat transfer function in the Y direction as shown by reference numeral 44. From two outer surfaces of the main backing 22 that intersect the Y direction (i.e., two side surfaces), heat is transferred to the shell head. To explain in more detail, heat generated in the electronic circuit 37 (and the two-dimensional transducer array) is transferred to the shell via the auxiliary backing 21 and the main backing 22, and this heat is absorbed by the shell. It is noted that in the present specification, perpendicular arrangement is one form of intersecting arrangement.

The first thermal anisotropic property possessed by the auxiliary backing 21 is characteristic in the Y direction, which is the low thermal conductivity direction. The second thermal anisotropic property possessed by the main backing 22 is characteristic in the X direction, which is the low thermal conductivity direction. The two low thermal conductivity directions are perpendicular to each other.

The thickness of the auxiliary backing 21 is smaller than the thickness of the main backing. The thickness of the auxiliary backing 21 is, for example, within a range from 1 to 5 mm. The thickness of the main backing is, for example, within a range from 10 to 15 mm.

In the configuration example shown in the drawing, the width of the auxiliary backing 21 in the Y direction and the width of the main backing 22 in the Y direction are identical. These widths are, for example, within a range from 10 to 20 mm. The width of the auxiliary backing 21 in the X direction is larger than the width of the main backing 22 in the X direction. More specifically, the auxiliary backing 21 overhangs on both sides in the X direction respectively by lengths corresponding to d1 and d2. Immediately below each of the overhang portions, a slit-shaped space is formed. The width of the auxiliary backing 21 in the X direction is, for example, within a range from 30 to 45 mm.

Each of the auxiliary backing 21 and the main backing 22 may be composed of a graphite block containing a plurality of graphene sheets. In the graphite block, each graphene sheet is composed of a large number of carbon atoms in a planar arrangement (in an i direction and a j direction). In the graphite block, the direction in which the graphene sheets are arranged is a k direction. Here, the i direction, the j direction, and the k direction have a perpendicular relationship with each other. A carbon block containing a plurality of planar graphite aggregates (see, for example, WO 2018/074493 A) may also be used as a backing.

The above-described graphite block has good ultrasound attenuation characteristics and good heat conduction characteristics. For example, thermal conductivity values in the above-noted i direction and j direction are within a range from 700 to 1000 (W/m/K), and a thermal conductivity value in the above-noted k direction is within a range from 10 to 20 (W/m/K). Materials for adjusting acoustic impedance and ultrasound attenuation may be added in the graphite block. It is also possible to use a graphite block having i-direction and j-direction thermal conductivity values exceeding 1000 (W/m/K), or a graphite block having i-direction and j-direction thermal conductivity values below 700 (W/m/K).

In an example case where only the IC 38 has emitted a large amount of heat in the electronic circuit 37, according to the present embodiment, the heat naturally diffuses in the X direction in the course of this heat being transferred to the auxiliary backing 21. This allows to avoid heat retention immediately below the IC 38. The heat that has diffused inside the auxiliary backing 21 is introduced into the main backing 22. The introduced heat is guided in the Y direction inside the main backing 22. The guided heat moves to the shell via the two heat output surfaces. The heat that has entered the shell spreads to the entire shell. The heat is transferred via the outer surfaces of the shell to the resin housing, and from the entire outer surfaces of the resin housing, the heat is discharged to the outside. The heat is also transferred from the shell to the probe cable, and discharged outside via the probe cable.

Each of the auxiliary backing 21 and the main backing 22 exhibits an extremely high heat transfer effect except in a specific direction. Accordingly, by means of the above-described heat transfer mechanism provided inside the ultrasound probe, heat generated in the electronic circuit 37 and the two-dimensional transducer array can be efficiently dissipated outside, and the temperature of the ultrasound transmission/reception surface placed in contact with the living body can be effectively decreased.

Figure 3:
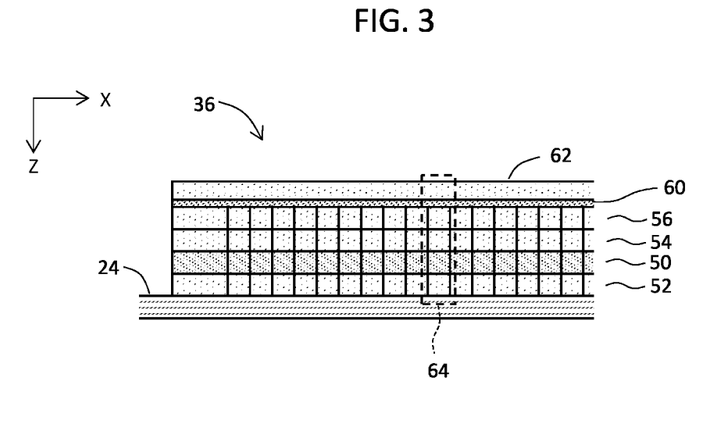
FIG. 3 is a cross-sectional view showing a laminate member.

FIG. 3 shows the laminate member 36. The laminate member 36 is composed of a reflection layer 52, a piezoelectric layer 50, a first matching layer 54, a second matching layer 56, a ground layer 60, and a third matching layer 62, which are laminated in the Z direction.

The piezoelectric layer 50 is composed of a plurality of piezoelectric elements arranged two-dimensionally. Each piezoelectric element is an electroacoustic transducer. The reflection layer 52 is composed of a plurality of reflection elements arranged two-dimensionally. Each reflection element is electrically conductive. The reflection layer 52 may also be referred to as a hard backing layer. The first matching layer 54 is composed of a plurality of first matching elements arranged two-dimensionally. Each first matching element is electrically conductive. The second matching layer 56 is composed of a plurality of second matching elements arranged two-dimensionally. Each second matching element is electrically conductive. On top of the second matching layer 56, the ground layer 60 is provided. The third matching layer 62 is provided on top of the ground layer 60. A protective layer, which is not shown in drawing, is provided on top of the third matching layer 62. The FPC 24 is provided below the reflection layer 52. Reference numeral 64 indicates one transducer or a portion including one transducer.

Figure 4:
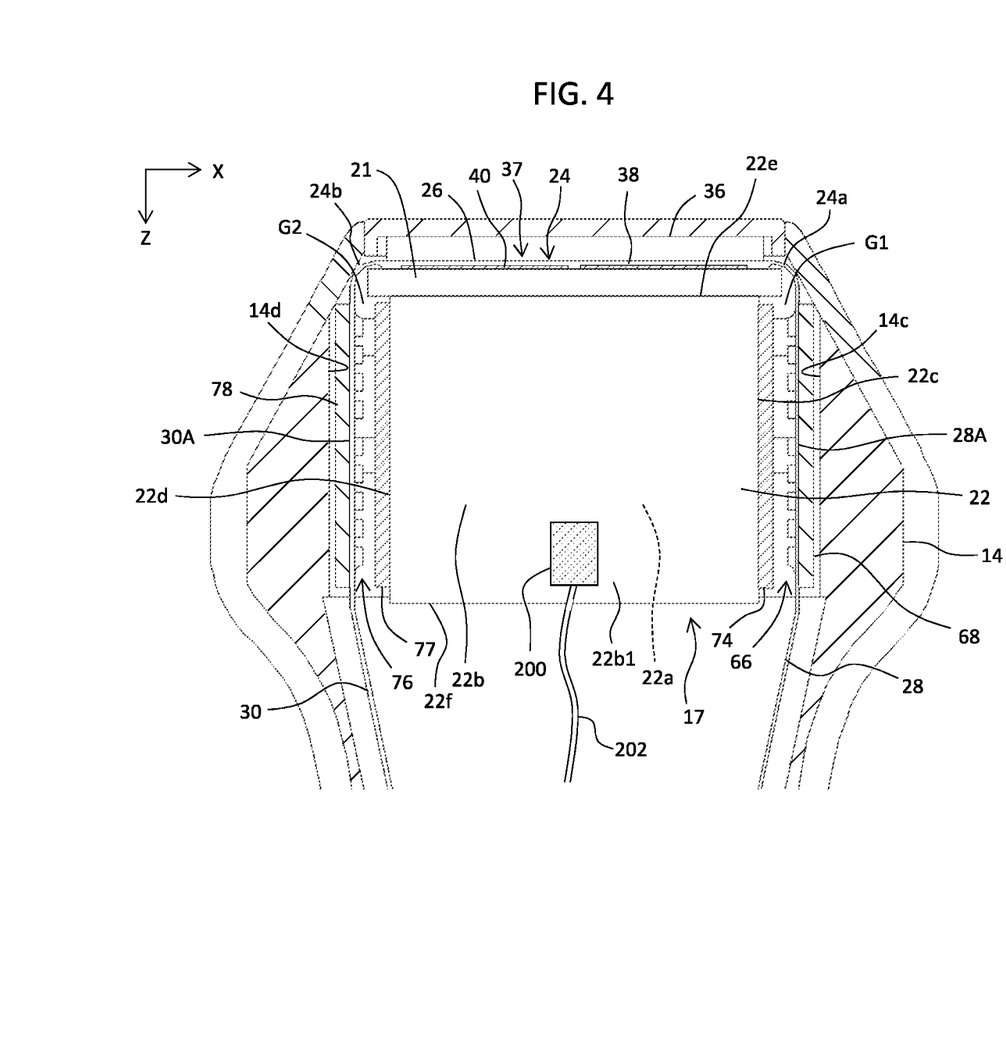
FIG. 4 is a XZ cross-sectional view showing a tip part of the ultrasound probe according to the embodiment.

FIG. 4 shows an XZ cross section of the tip part of the ultrasound probe according to the embodiment. The transducer assembly 17 is arranged inside the shell head 14. The transducer assembly 17 includes the laminate member 36, the electronic circuit 37, the auxiliary backing 21, and the main backing 22, which are arranged in the Z direction. The FPC 24, which is a wiring member, is formed having the horizontal part 26, the first hanging part 28, and the second hanging part 30. The horizontal part 26 is sandwiched between the laminate member 36 and the electronic circuit 37. In the configuration example shown in the drawing, the electronic circuit 37 is composed of the two ICs 38, 40 arranged in the X direction.

The auxiliary backing 21 has two outer surfaces (i.e., two side surfaces) perpendicular to the Y direction (i.e., the direction into the drawing sheet plane) and two outer surfaces (i.e., two side surfaces) perpendicular to the X direction. Each of these four side surfaces is an exposed surface that does not exhibit a heat transfer effect. The first bent portion 24a of the FPC 24 curves around one end portion, in the X direction, of the auxiliary backing 21. The second bent portion 24b of the FPC 24 curves around the other end portion, in the X direction, of the auxiliary backing 21.

In the auxiliary backing 21, the direction in which the graphene sheets are arranged is the Y direction. The one end portion and the other end portion of the auxiliary backing 21 in the X direction are not likely to be deformed in the X direction. Accordingly, even when a force (or shear force) is applied to the one end portion by the first bent portion 24a, the one end portion is not easily deformed. Similarly, even when a force (or shear force) is applied to the other end portion by the second bent portion 24b, the other end portion is not easily deformed.

The main backing 22 has two outer surfaces (i.e., two side surfaces) 22a, 22b perpendicular to the Y direction (i.e., the direction into the drawing sheet plane) and two outer surfaces (i.e., two side surfaces) 22c, 22d perpendicular to the X direction. Each of the two outer surfaces 22a, 22b perpendicular to the Y direction is, in relative terms, a high thermal conductivity surface, and functions as a heat output surface. Each of the two outer surfaces 22c, 22d perpendicular to the X direction is, in relative terms, a low thermal conductivity surface. Each of the outer surfaces 22c, 22d does not exhibit a heat transfer effect. In the main backing 22, the direction in which the graphene sheets are arranged is the X direction.

The shell head 14 has a shape that surrounds the transducer assembly 17, and retains the transducer assembly 17. The shell head 14 has two inner surfaces perpendicular to the Y direction and two inner surfaces perpendicular to the X direction. Each of the two inner surfaces perpendicular to the Y direction functions as a heat input surface.

The two outer surfaces 22a, 22b of the main backing 22 perpendicular to the Y direction are joined to the two inner surfaces of the shell head 14 perpendicular to the Y direction. Via two interfaces formed by the joining, heat moves from the main backing 22 to the shell head 14. Between the two outer surfaces 22c, 22d of the main backing 22 perpendicular to the X direction and the two inner surfaces 14c, 14d of the shell head 14 perpendicular to the X direction, gaps G1, G2 are formed. Each of the gaps G1, G2 has a shape of a slit. The gap G1 includes the space present immediately below the first overhang portion of the auxiliary backing 21.

The gap G2 includes the space present immediately below the second overhang portion of the auxiliary backing 21.

The first hanging part 28 has a first vertical portion 28A, which is the upper end portion. The first vertical portion 28A extends through the gap G1. On the inner surface (i.e., the surface toward the main backing) of the first vertical portion 28A, a first group of electric components 66 is provided. The first group of electric components 66 is composed of a plurality of electric components arranged in the Y direction and the Z direction. More specifically, the first group of electric components 66 includes a plurality of capacitors necessary for operation of the electronic circuit 37.

Between the first group of electric components 66 and the outer surface 22c of the main backing 22, an electrical insulation plate 74 is provided, which is an electrical insulation member. With this, electrical short circuit between the main backing 22 and the first group of electric components 66 is prevented. The electrical insulation plate 74 is adhered to the first group of electric components 66, or is adhered to the main backing 22.

To the outer surface (i.e., the surface toward the inner surface 14c) of the first vertical portion 28A, a reinforcement plate 68 is adhered, which is a reinforcement member. The reinforcement plate 68 may further be fixed to the inner surface 14c using a double-sided tape or the like. The reinforcement plate 68 is composed of, for example, an insulating member.

The second hanging part 30 has a second vertical portion 30A, which is the upper end portion. The second vertical portion 30A extends through the gap G2. On the inner surface (i.e., the surface toward the main backing) of the second vertical portion 30A, a second group of electric components 76 is provided. The second group of electric components 76 is composed of a plurality of electric components arranged in the Y direction and the Z direction. More specifically, the second group of electric components 76 includes a plurality of capacitors necessary for operation of the electronic circuit 37.

Between the second group of electric components 76 and the outer surface 22d of the main backing 22, an electrical insulation plate 77 is provided, which is an electrical insulation member. With this, electrical short circuit between the main backing 22 and the second group of electric components 76 is prevented. The electrical insulation plate 77 is adhered to the second group of electric components 76, or is adhered to the main backing 22.

To the outer surface (i.e., the surface toward the inner surface 14d) of the second vertical portion 30A, a reinforcement plate 78 is adhered, which is a reinforcement member. The reinforcement plate 78 may further be fixed to the inner surface 14d using a double-sided tape or the like. The reinforcement plate 78 is composed of, for example, an insulating member.

The upper surface 22e of the main backing 22 is joined to the lower surface of the auxiliary backing 21. The lower surface 22f of the main backing 22 is an exposed surface. As will be described later, a sound absorbing member or a heat transfer member may be provided on the lower surface 22f.

On the outer surface 22b that functions as a heat output surface, a temperature sensor 200 is provided. More specifically, the temperature sensor 200 is provided on the outer surface 22b at its part 22b1 located centrally in the X direction and toward the lower end. The temperature sensor 200 is composed of, for example, a thermistor. A signal line 202 is drawn out of the temperature sensor 200. The signal line 202 is connected to the FPC 24 or to a signal line inside the probe cable not shown in drawing. A plurality of temperature sensors may be provided on the outer surface 22b. Temperature sensors may be respectively provided on the outer surface 22a and the outer surface 22b.

By providing the temperature sensor 200, it becomes possible to monitor the temperature of the main backing or, in particular, the temperature of the interface between the main backing and the shell head. This makes it possible to manage the surface temperature of the ultrasound probe or, in particular, the surface temperature of the ultrasound transmission/reception surface.

In the present embodiment, the gaps G1, G2 are reserved on both sides of the main backing in the X direction. The FPC 24 extends through the gaps G1, G2. By using the gaps G1, G2, the first group of electric components 66 and the second group of electric components 76 are arranged at positions near the electronic circuit 37.

Figure 5:
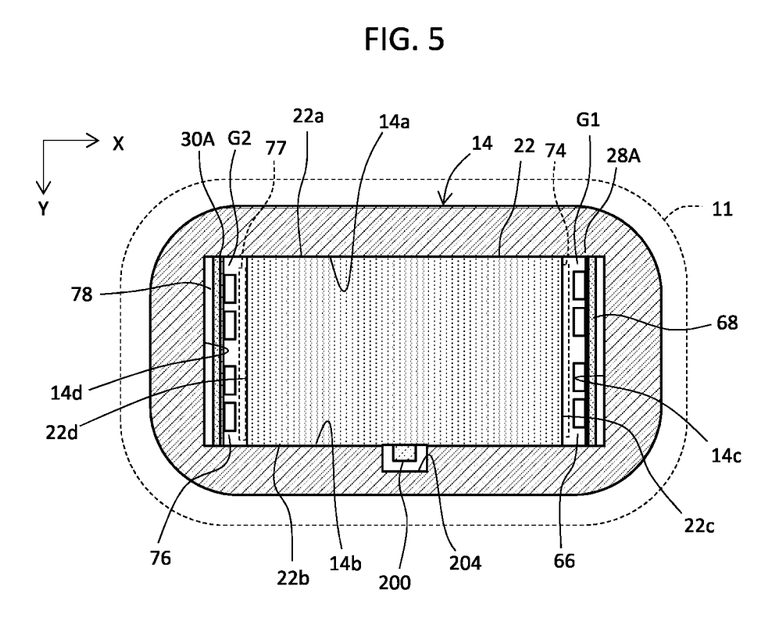
FIG. 5 is a schematic view showing an XY cross section of the tip part of the ultrasound probe according to the embodiment.

FIG. 5 is a schematic view showing an XY cross section of the tip part of the ultrasound probe. The main backing 22 has the two outer surfaces 22a, 22b perpendicular to the Y direction, and also the two outer surfaces 22c, 22d perpendicular to the X direction. The shell head 14 has the two inner surfaces 14a, 14b perpendicular to the Y direction, and also the two inner surfaces 14c, 14d perpendicular to the X direction.

The outer surface 22a and the inner surface 14a are joined, and the outer surface 22b and the inner surface 14b are joined. The gap G1 is formed between the outer surface 22c and the inner surface 14c. The gap G2 is formed between the outer surface 22d and the inner surface 14d. In the gap G1, the first vertical portion 28A, the first group of electric components 66, the electrical insulation plate 74, and the reinforcement plate 68 are arranged. In the gap G2, the second vertical portion 30A, the second group of electric components 76, the electrical insulation plate 77, and the reinforcement plate 78 are arranged.

In the shell head 14, a recess 204 is formed. The opening of the recess 204 constitutes part of the inner surface 14b. The space inside the recess 204 functions as a receiving chamber that receives the temperature sensor 200. Walls of the recess 204 are spaced from the temperature sensor 200. The temperature sensor 200 is in contact with only the outer surface 22b of the main backing 22.

In general, machining of a backing having thermal anisotropy is difficult; in other words, it is difficult to form a recess in the main backing 2. In view of this, in the present embodiment, the recess 204 is formed in the shell head 14, and the temperature sensor 200 is received therein. Since the shell head 14 is not directly in contact with the temperature sensor 200, the temperature of the heat output surface can be correctly measured by the temperature sensor 200.

In the present embodiment, each of the outer surfaces 22a, 22b, 22c, 22d is a planar surface. The entirety or a part of each of the outer surfaces 22a, 22b, 22c, 22d may be a curved surface. Likewise, in the present embodiment, each of the inner surfaces 14a, 14b, 14c, 14d is a planar surface. The entirety or a part of each of the inner surfaces 14a, 14b, 14c, 14d may be a curved surface.

Figure 6:
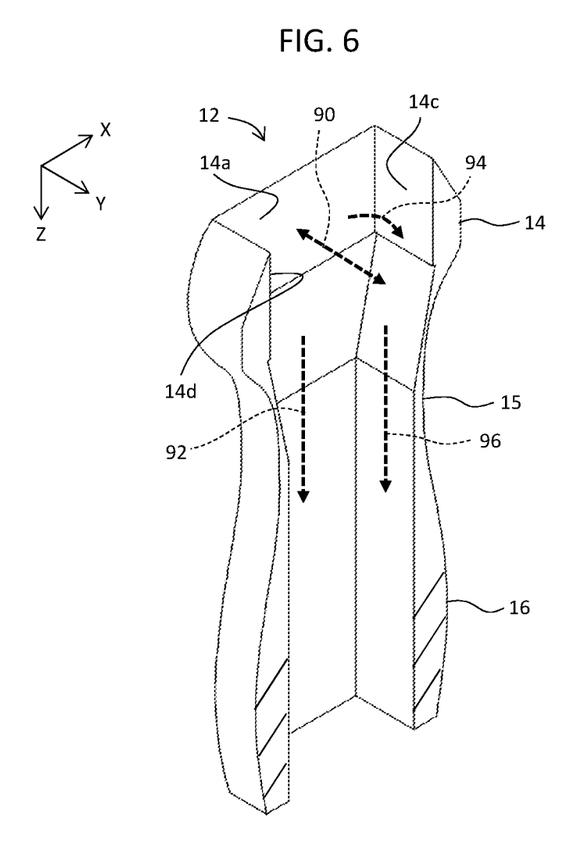
FIG. 6 is a perspective view showing a shell.

FIG. 6 shows the shell 12. As noted earlier, the shell 12 is formed having the shell head 14, the middle part 15, and the rear end part 16. The shell head 14 has the two inner surfaces perpendicular to the Y direction (while only one inner surface 14a is shown in FIG. 6), and the two inner surfaces 14c, 14d perpendicular to the X direction. Heat from the main backing flows into the shell head 14 via the two inner surfaces perpendicular to the Y direction (see reference numeral 90). This heat diffuses in the shell head 14 (see reference numeral 94), and simultaneously diffuses to the entire shell 12 (see reference numerals 92 and 96). The heat diffused in the shell 12 is discharged outside via the resin housing, and is also discharged outside via the probe cable.

Figure 7:
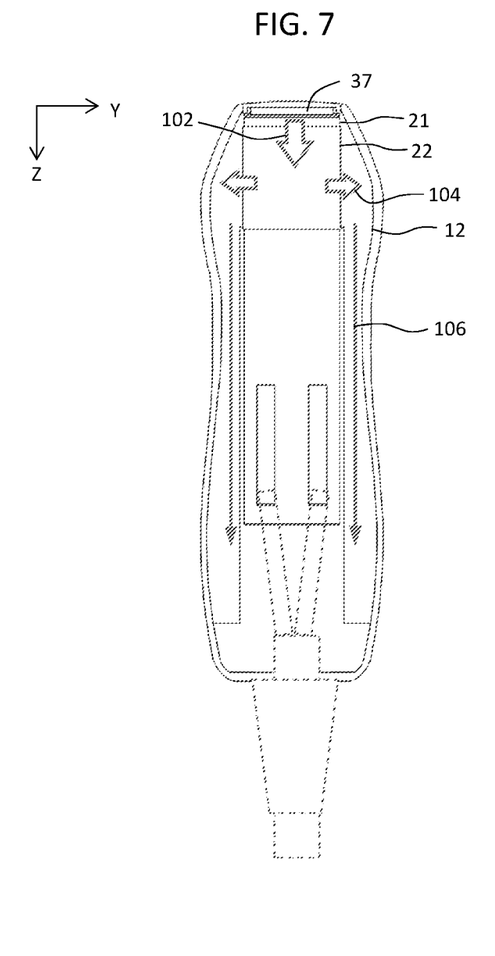
FIG. 7 is an YZ cross-sectional view showing the ultrasound probe according to the embodiment.

FIG. 7 shows a YZ cross section of the ultrasound probe. Reference numeral 102 indicates the direction of movement of heat generated in the electronic circuit 37 and the two-dimensional transducer array. The heat moves through the auxiliary backing 21 to the main backing 22. Reference numeral 104 indicates movement, in the Y direction, of the heat that has flowed into the main backing 22, whereby the heat flows into the shell 12. Reference numeral 106 indicates the direction of heat movement (or diffusion) inside the shell 12.

It is noted that FIG. 7 shows the probe cable, a bundle of signal lines inside the probe cable, and connectors connected to the bundle of signal lines. The connectors connected to the bundle of signal lines are connected to connectors provided in the FPC.

Figure 8:
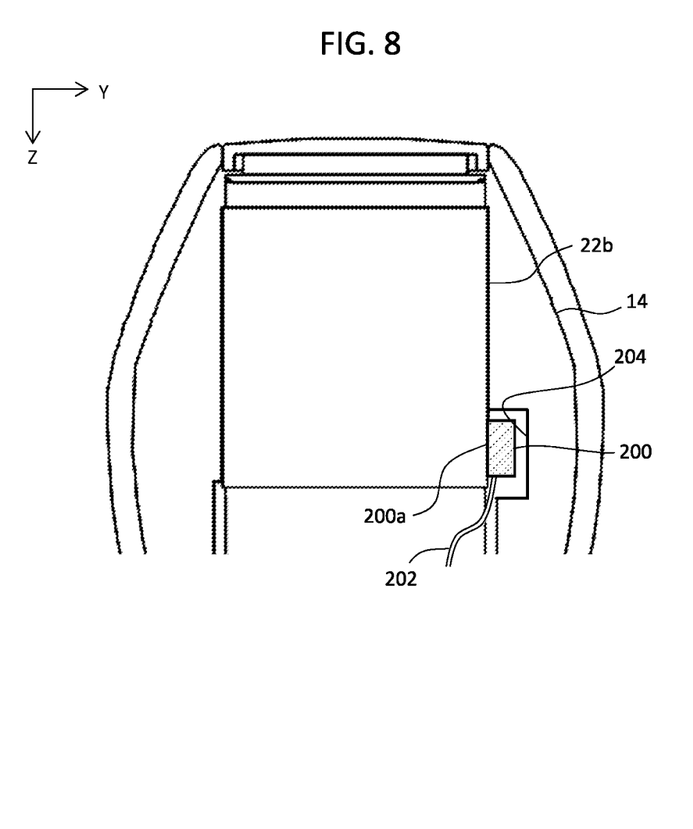
FIG. 8 is an YZ cross-sectional view showing an arrangement of a temperature sensor.

FIG. 8 shows a YZ cross section of the tip portion of the ultrasound probe. As noted earlier, the recess 204 is formed in the shell head 14. The space inside the recess 204 is the receiving chamber for the temperature sensor 200. Inner surfaces of the recess 204 are spaced from the temperature sensor 200.

A detection surface 200a of the temperature sensor 200 is joined to the outer surface 22b of the main backing. The position at which the temperature sensor 200 is joined is more specifically a part of the outer surface 22b that corresponds to a central portion in the X direction and a lower end portion in the Z direction. The signal line 202 is drawn out of the temperature sensor 200. The lower surface of the main backing is also a high thermal conductivity surface. A temperature sensor may be arranged on this lower surface.

Figure 9:
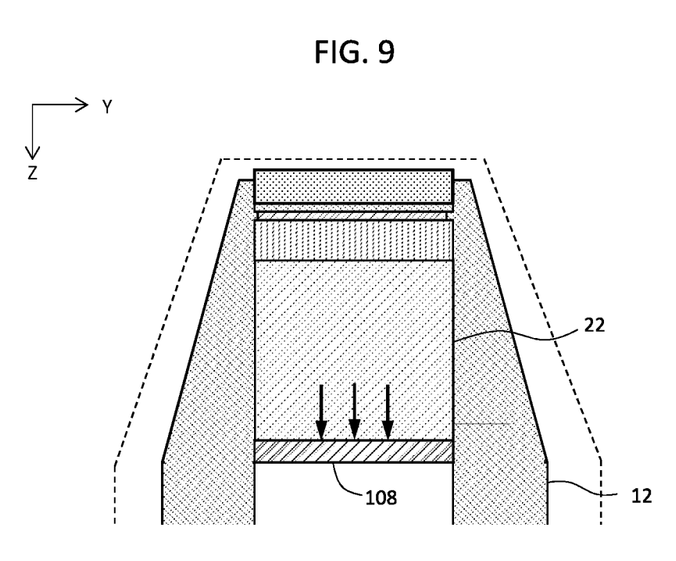
FIG. 9 is a diagram showing a first modified embodiment.

Modified embodiments will now be described using FIGS. 9 and 10. FIG. 9 shows a first modified embodiment. A sound absorbing plate 108 is provided under the main backing 22. More specifically, the sound absorbing plate 108 is joined to the lower surface of the main backing. When ultrasound waves are not completely attenuated inside the main backing 22, the ultrasound waves are reflected at the lower surface of the main backing 22, and the reflected waves generated thereby may possibly return to the two-dimensional transducer array. Such reflected waves degrade the image quality of ultrasound images. By providing the sound absorbing plate 108 on the lower surface of the main backing 22, generation of the above-described reflected waves can be effectively suppressed.

Figure 10:
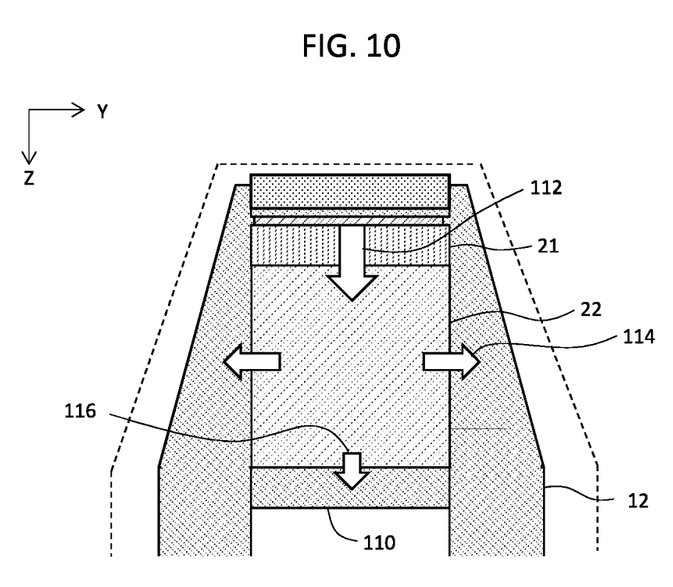
FIG. 10 is a diagram showing a second modified embodiment.

FIG. 10 shows a second modified embodiment. A heat transfer plate 110 is provided under the main backing 22. More specifically, the heat transfer plate 110 is joined to the lower surface of the main backing 22. Heat generated in the electronic circuit and the like moves to the main backing 22 via the auxiliary backing 21 as shown by an arrow 112. The heat that has flowed into the main backing 22 moves from the main backing 22 directly to the shell 12 as shown by an arrow 114, and also moves from the main backing 22 to the shell 12 via the heat transfer plate 110 as shown by an arrow 116. The lower surface of the main backing 22 is a high thermal conductivity surface. Accordingly, efficiency of heat transfer from the main backing 22 to the shell 12 can be further increased according to the second modified embodiment.

According to the above-described embodiments, heat generated in the electronic circuit and the like can be guided to the heat absorbing member via a path having an extremely high thermal conductivity inside the backing member. It is thereby possible to effectively suppress the temperature of the ultrasound transmission/reception surface placed in contact with the living body. Further, since two gaps can be reserved near the main backing, those gaps can be used to arrange wiring members and groups of electric components. Both of the two side surfaces bordering the two gaps are low thermal conductivity surfaces, so that the groups of electric components can be thermally protected. Further, since the auxiliary backing is provided on top of the main backing, and orientations of the two backings are perpendicular to each other, heat can first be diffused in the X direction in the auxiliary backing, and can subsequently be guided in the Y direction in the main backing. In addition, since the temperature sensor is arranged on a high thermal conductivity surface of the main backing, and the temperature sensor is spaced from the shell, the temperature of the main backing can be correctly detected, or in other words, heat transport effect of the main backing can be correctly measured.

In the above-described embodiments, the auxiliary backing may be eliminated. In that case, the electronic circuit is provided on the upper surface of the main backing. Further, in above-described embodiments, the backing member may be composed of three or more backings. When the laminate member has a cylindrical plate shape, the upper surface of the backing member is formed to have a cylindrical plate shape. As a backing having thermal anisotropy, backings other than those described above may be used. For example, it is possible to use a backing in which a plurality of heat transfer layers and a plurality of spacers are alternately laminated.

The invention claimed is:

1. An ultrasound probe, comprising:
a transducer array;
an electronic circuit provided behind the transducer array and electrically connected to the transducer array;
a sheet-shaped wiring member electrically connected to the electronic circuit;
a backing provided behind the electronic circuit and configured to attenuate ultrasound waves from the transducer array; and
a heat absorbing member configured to absorb heat from the backing,
wherein assuming that a direction in which the transducer array, the electronic circuit, and the backing are arranged is defined as a Z direction, a direction perpendicular to the Z direction is defined as an X direction, and a direction perpendicular to the Z direction and the X direction is defined as a Y direction,
in the backing, both of Z-direction thermal conductivity and Y-direction thermal conductivity are higher than X-direction thermal conductivity,
the backing has two outer surfaces intersecting the X direction and bordering a first gap and a second gap, and
the wiring member extends through the first gap and the second gap.

2. The ultrasound probe according to claim 1, wherein the heat absorbing member has two inner surfaces that face the two outer surfaces intersecting the X direction, and
two gaps between the two outer surfaces and the two inner surfaces are the first gap and the second gap.

3. The ultrasound probe according to claim 1, wherein the wiring member includes:
a horizontal part provided between the transducer array and the electronic circuit;

a first vertical portion connected to one end portion of the horizontal part via a first bent portion; and a second vertical portion connected to the other end portion of the horizontal part via a second bent portion, the first vertical portion extends through the first gap, and the second vertical portion extends through the second gap.

4. The ultrasound probe according to claim 3, further including:

a first group of electric components arranged on the first vertical portion and received in the first gap; and a second group of electric components arranged on the second vertical portion and received in the second gap.

5. The ultrasound probe according to claim 4, wherein the two outer surfaces intersecting the X direction are a first outer surface and a second outer surface, the first vertical portion has a first face side which faces the first outer surface and on which the first group of electric components are arranged, and a first back side located opposite to the first face side, the second vertical portion has a second face side which faces the second outer surface and on which the second group of electric components are arranged, and a second back side located opposite to the second face side, a first electrical insulation member is provided between the first outer surface and the first group of electric components, and a second electrical insulation member is provided between the second outer surface and the second group of electric components.

6. The ultrasound probe according to claim 5, further including:

a first reinforcement member joined to the first back side; and a second reinforcement member joined to the second back side.

7. The ultrasound probe according to claim 1, wherein the backing has two outer surfaces intersecting the Y direction, and the heat absorbing member has two inner surfaces joined to the two outer surfaces intersecting the Y direction.

8. The ultrasound probe according to claim 1, wherein the backing comprises an auxiliary backing provided behind the electronic circuit and configured to diffuse heat in the X direction, and a main backing provided behind the auxiliary backing and configured to transfer heat in the Y direction, and a thickness of the auxiliary backing in the Z direction is less than a thickness of the main backing in the Z direction.

9. The ultrasound probe according to claim 8, wherein the main backing has two outer surfaces intersecting the X direction and bordering the first gap and the second gap.

10. The ultrasound probe according to claim 8, wherein the first gap includes space formed immediately below one end portion, in the X direction, of the auxiliary backing, and the second gap includes space formed immediately below the other end portion, in the X direction, of the auxiliary backing.

11. The ultrasound probe according to claim 8, wherein the wiring member includes a first bent portion curving around one end portion, in the X direction, of the auxiliary backing, and a second bent portion curving around the other end portion, in the X direction, of the auxiliary backing.

12. The ultrasound probe according to claim 1, wherein the wiring member includes a horizontal part provided between the transducer array and the electronic circuit, a first vertical portion connected to one end portion of the horizontal part via a first bent portion, and a second vertical portion connected to the other end portion of the horizontal part via a second bent portion.

13. The ultrasound probe according to claim 1 further comprising a shell having a shell head that retains the backing and configured to absorb heat from the backing.

14. The ultrasound probe according to claim 13, wherein the shell head has a shape that surrounds the backing.

15. The ultrasound probe according to claim 14, wherein the shell head has two inner surfaces spaced from the two outer surfaces.

16. The ultrasound probe according to claim 13, further comprising a probe cover having an inner surface joined to an outer surface of the shell.

17. The ultrasound probe according to claim 1 further comprising a temperature sensor arranged on at least one of the two outer surfaces.

18. The ultrasound probe according to claim 17, wherein the outer surface on which the temperature sensor is arranged has an upper end portion located near the electronic circuit, and a lower end portion located away from the electronic circuit, and the temperature sensor is arranged at the lower end portion.

* * * * *